United States Patent
Georgeson et al.

(10) Patent No.: US 9,395,335 B2
(45) Date of Patent: Jul. 19, 2016

(54) ULTRASONIC INSPECTION SYSTEM FOR NON-PLANAR SURFACES

(71) Applicant: The Boeing Company, Chicago, IL (US)

(72) Inventors: Gary Ernest Georgeson, Tacoma, WA (US); William Joseph Tapia, Graham, WA (US); Justin D. Serrill, Issaquah, WA (US)

(73) Assignee: THE BOEING COMPANY, Chicago, IL (US)

( * ) Notice: Subject to any disclaimer, the term of this patent is extended or adjusted under 35 U.S.C. 154(b) by 287 days.

(21) Appl. No.: 13/941,884

(22) Filed: Jul. 15, 2013

(65) Prior Publication Data

US 2015/0013463 A1    Jan. 15, 2015

(51) Int. Cl.
   *G01N 29/04*   (2006.01)
   *G01N 29/22*   (2006.01)
   *G01N 29/265*  (2006.01)

(52) U.S. Cl.
   CPC ............ *G01N 29/043* (2013.01); *G01N 29/225* (2013.01); *G01N 29/265* (2013.01); *G01N 2291/0231* (2013.01); *G01N 2291/044* (2013.01); *G01N 2291/106* (2013.01); *G01N 2291/2638* (2013.01); *G01N 2291/2694* (2013.01)

(58) Field of Classification Search
   CPC .................... G01N 2291/2638; G01N 29/043; G01N 29/265; G01N 29/225; G01N 2291/2694; G01N 2291/106; G01N 2291/044
   USPC .............................. 73/628, 642, 622, 640, 644
   See application file for complete search history.

(56) References Cited

U.S. PATENT DOCUMENTS

| | | | | | |
|---|---|---|---|---|---|
| 3,964,296 | A | * | 6/1976 | Matzuk | 73/607 |
| 5,549,004 | A | * | 8/1996 | Nugent | 73/622 |
| 5,798,461 | A | * | 8/1998 | Banta et al. | 73/625 |
| 5,804,728 | A | * | 9/1998 | Beall | G01N 29/07 73/598 |
| 7,249,512 | B2 | * | 7/2007 | Kennedy | G01N 29/225 73/618 |
| 8,590,381 | B2 | * | 11/2013 | Murai et al. | 73/602 |
| 2004/0093949 | A1 | * | 5/2004 | Alleyne | B61K 9/10 73/625 |
| 2007/0044564 | A1 | * | 3/2007 | Bui | G01N 29/043 73/618 |
| 2010/0095775 | A1 | * | 4/2010 | Sarr et al. | 73/621 |
| 2014/0137650 | A1 | * | 5/2014 | Kleinert | G01N 29/043 73/628 |

FOREIGN PATENT DOCUMENTS

EP        1830185 A1    9/2007

OTHER PUBLICATIONS

Cyr, "Ultrasound Phased Array," NDT.net, vol. 7, No. 05, May 2002, 4 pages, accessed Jul. 12, 2013. http://www.ndt.net/article/v07n05/rdtech/rdtech.htm.
Extended European Search Report, dated Sep. 18, 2015, regarding Application No. EP14176410.0, 7 pages.

* cited by examiner

*Primary Examiner* — John Fitzgerald
*Assistant Examiner* — Suman K Nath
(74) *Attorney, Agent, or Firm* — Yee & Associates, P.C.

(57) ABSTRACT

A method and apparatus for inspecting a test object. A sound signal is sent from a first portion of a curved transducer array through the test object in a direction towards a second portion of the curved transducer array. The curved transducer array has a shape that is configured to cover a non-planar surface of the test object. A response signal in response to the sound signal is received at the second portion of the curved transducer array.

18 Claims, 14 Drawing Sheets

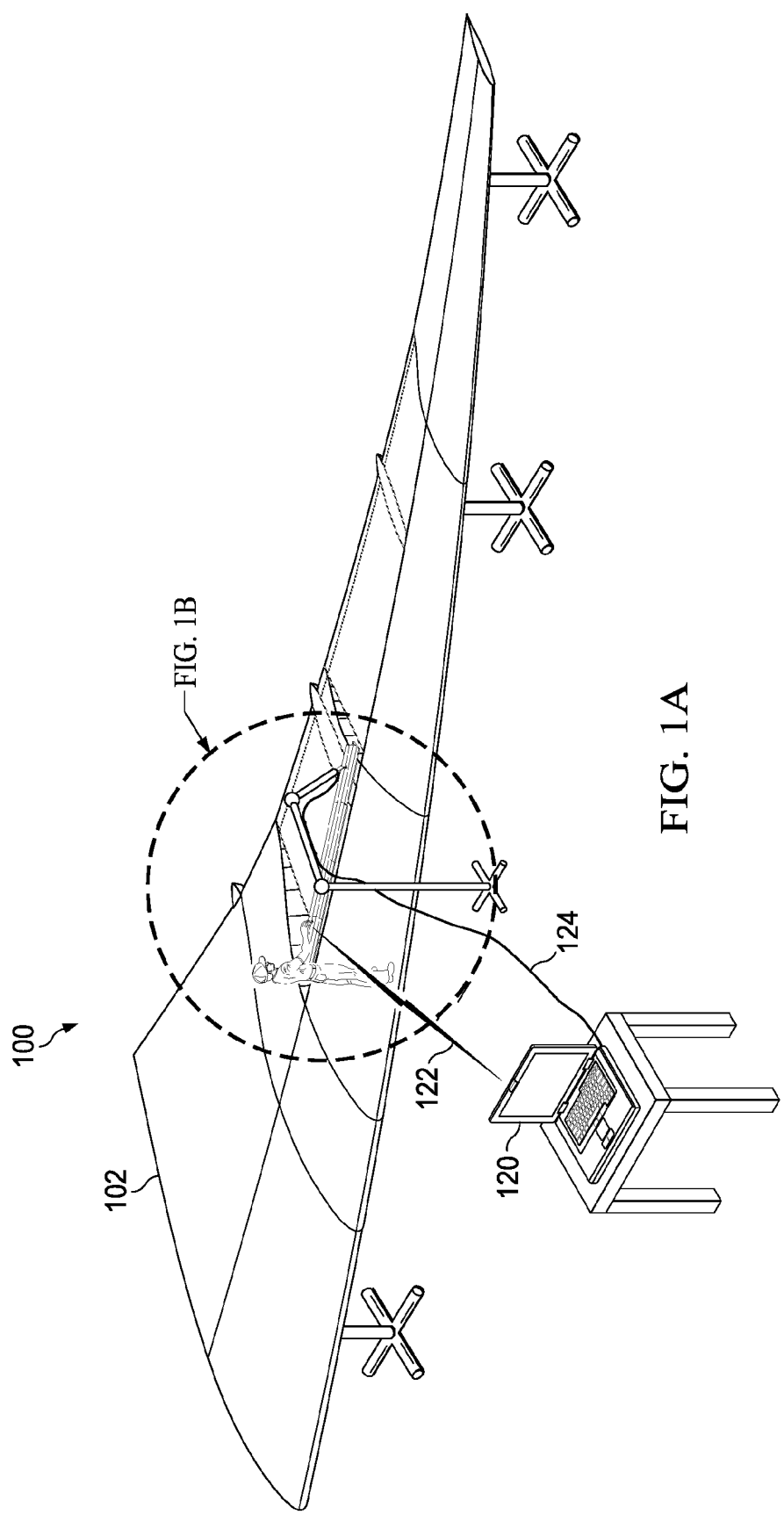

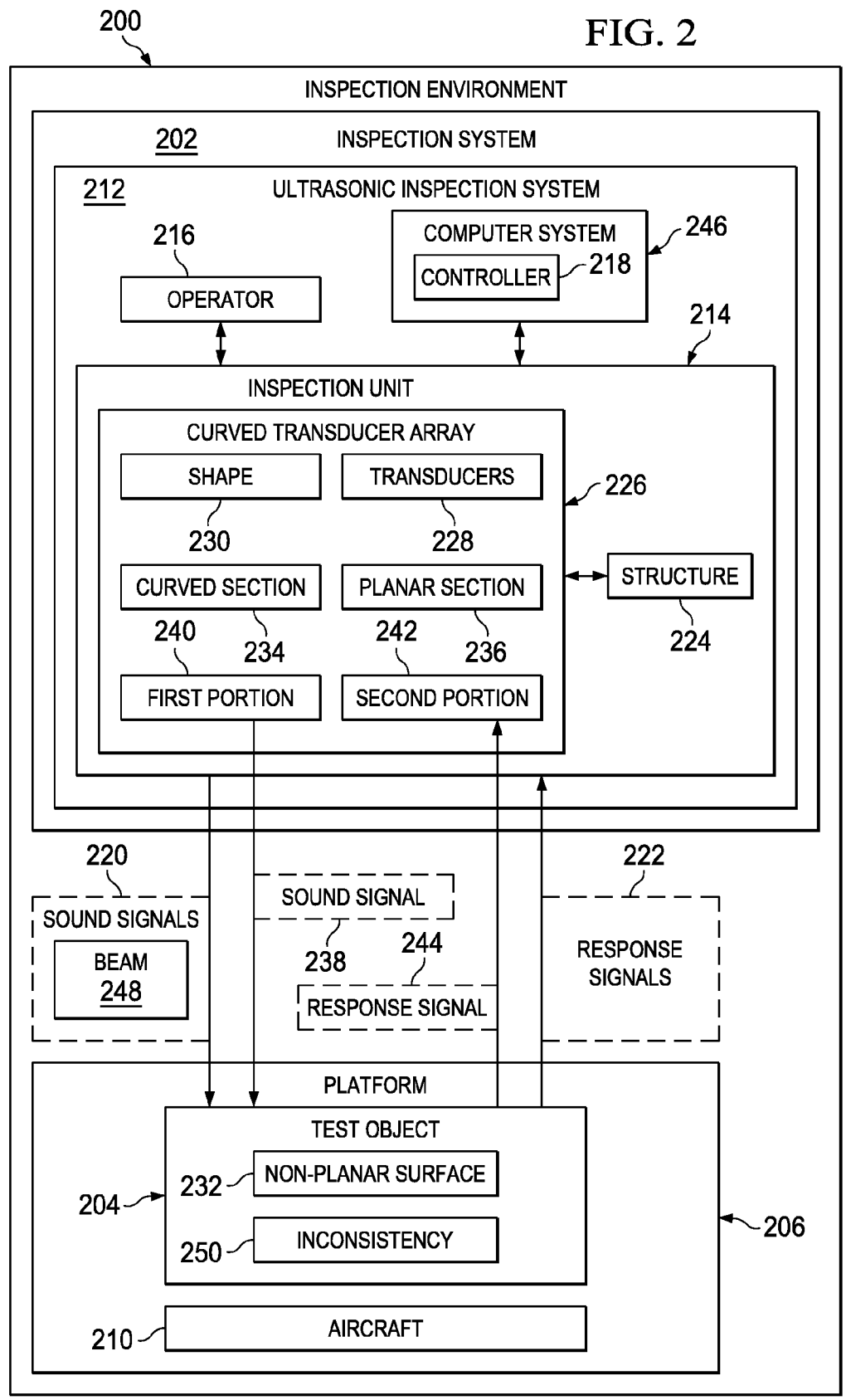

ured and cured to form the final composite structure of an illustrative embodiment of the present disclosure when

ULTRASONIC INSPECTION SYSTEM FOR NON-PLANAR SURFACES

BACKGROUND INFORMATION

1. Field

The present disclosure relates generally to composite structures and, in particular, to inspecting composite structures. Still more particularly, the present disclosure relates to a method and apparatus for inspecting composite structures with non-planar surfaces.

2. Background

Aircraft are being designed and manufactured with greater and greater percentages of composite materials. Composite materials are used in aircraft to decrease the weight of the aircraft. This decreased weight improves performance features such as payload capacity and fuel efficiency. Further, composite materials provide longer service life for various components in an aircraft.

Composite materials may be tough, light-weight materials created by combining two or more functional components. For example, a composite material may include reinforcing fibers bound in a polymer resin matrix. The fibers may be unidirectional or may take the form of a woven cloth or fabric. The fibers and resins may be arranged and cured to form a composite structure.

Using composite materials to create aerospace composite structures may allow for portions of an aircraft to be manufactured in larger pieces or sections. For example, a fuselage in an aircraft may be created in cylindrical sections to form the fuselage of the aircraft. Other examples include, without limitation, wing sections joined to form a wing or stabilizer sections joined to form a stabilizer.

In manufacturing composite structures, layers of composite material may be laid up on a tool. The layers of composite material may be comprised of fibers in sheets. These sheets may take the form of, for example, without limitation, fabrics, tape, tows, or other suitable configurations for the sheets. In some cases, resin may be infused or pre-impregnated into the sheets. These types of sheets are commonly referred to as prepreg.

The different layers of prepreg may be laid up in different orientations and different numbers of layers may be used depending on the desired thickness of the composite structure being manufactured. These layers may be laid up by hand or using automated lamination equipment such as a tape laminating machine or a fiber placement system.

After the different layers have been laid up on the tool, the layers may be consolidated and cured upon exposure to temperature and pressure, thus forming the final composite structure. Thereafter, the composite structure may be inspected to determine whether inconsistencies are present. The inspection may be performed using ultrasound testing, infrared testing, visual inspections, and other suitable types of testing.

This testing may be performed to identify various inconsistencies in the composite structure. With aircraft, many of the surfaces of the composite structures used in the aircraft may have shapes with curves, angles, or other complex contours. These types of surfaces may be more difficult than desired to inspect to determine whether inconsistencies are present.

Therefore, it would be desirable to have a method and apparatus that takes into account at least some of the issues discussed above, as well as other possible issues.

SUMMARY

In one illustrative embodiment, an apparatus comprises a curved transducer array. The curved transducer array has a shape that is configured to cover a non-planar surface of a test object and send a sound signal from a first portion of the curved transducer array through the test object to a second portion of the curved transducer array.

In another illustrative embodiment, an aircraft inspection system comprises a curved transducer array, a structure, and a controller. The curved transducer array has a shape that is configured to cover a non-planar surface of a test object and send a sound signal from a first portion of the curved transducer array through the test object to a second portion of the curved transducer array. The structure is physically associated with the curved transducer array. The controller is configured to control a transmission of the sound signal from the first portion of the curved transducer array. The controller is further configured to control a reception of the sound signal at the second portion of the curved transducer array to form a through-transmission of the sound signal.

In yet another illustrative embodiment, a method for inspecting a test object is presented. A sound signal is sent from a first portion of a curved transducer array through the test object in a direction towards a second portion of the curved transducer array. The curved transducer array has a shape that is configured to cover a non-planar surface of the test object. A response signal in response to the sound signal is received at the second portion of the curved transducer array.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIGS. 1A and 1B are illustrations of an inspection environment in accordance with an illustrative embodiment;

FIG. 2 is an illustration of a block diagram of an inspection environment in accordance with an illustrative embodiment;

DETAILED DESCRIPTION

The illustrative embodiments recognize and take into account one or more considerations. For example, the illustrative embodiments recognize and take into account that inspection of test objects with curved shapes may be more difficult than desired. For example, the illustrative embodiments recognize and take into account that parts, like the edges of stiffeners, have a surface with a non-planar shape. For example, the edge of a stiffener may have a bulb shape, an egg shape, a bull nose shape, or some other shape.

The illustrative embodiments recognize and take into account that with this type of shape, a response of a signal sent into that portion of the stiffener may not provide a desired response to analysis to determine whether an inconsistency is present. The illustrative embodiments recognize and take into account that when an array of transducers do not conform to the surfaces of the bulb, a through-transmission or other response on the bulb with good response signals may be more difficult than desired or may not be possible. The illustrative embodiments recognize and take into account that with the transducer devices, multiple passes may be needed for inspection on the edge of the stiffener.

Thus, the illustrative embodiments provide a method and apparatus for inspecting test objects. In one illustrative embodiment, an apparatus comprises a curved transducer array having a shape that is configured to cover a non-planar surface of a test object. The curved transducer array is configured to send a sound signal from a first portion of the curved transducer array through the test object to a second portion of the curved transducer array.

Figure 1B:
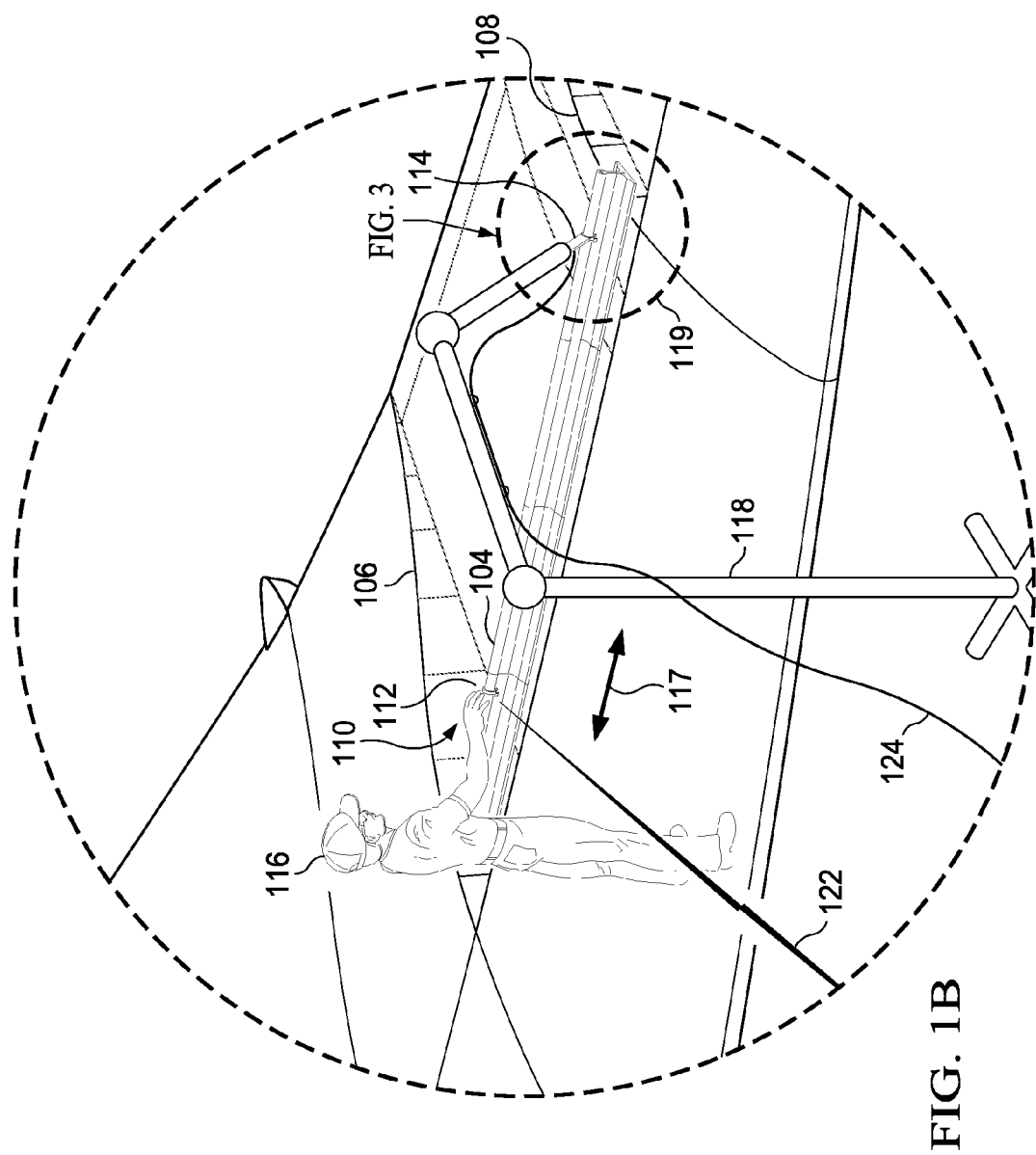

With reference now to the figures, and in particular with reference to FIGS. 1A and 1B, illustrations of an inspection environment are depicted in accordance with an illustrative embodiment. In this illustrative example, inspection environment 100 includes wing 102. In this example, wing 102 is partially assembled. As depicted, stiffener 104 extends between rib 106 and rib 108.

An inspection of stiffener 104 may be made using inspection system 110. Inspection system 110 includes inspection unit 112 and inspection unit 114. In these illustrative examples, inspection unit 112 and inspection unit 114 include curved transducer arrays (not shown). As depicted, inspection unit 112 is moved by human operator 116, while inspection unit 114 is moved by robotic operator 118.

Figure 3:
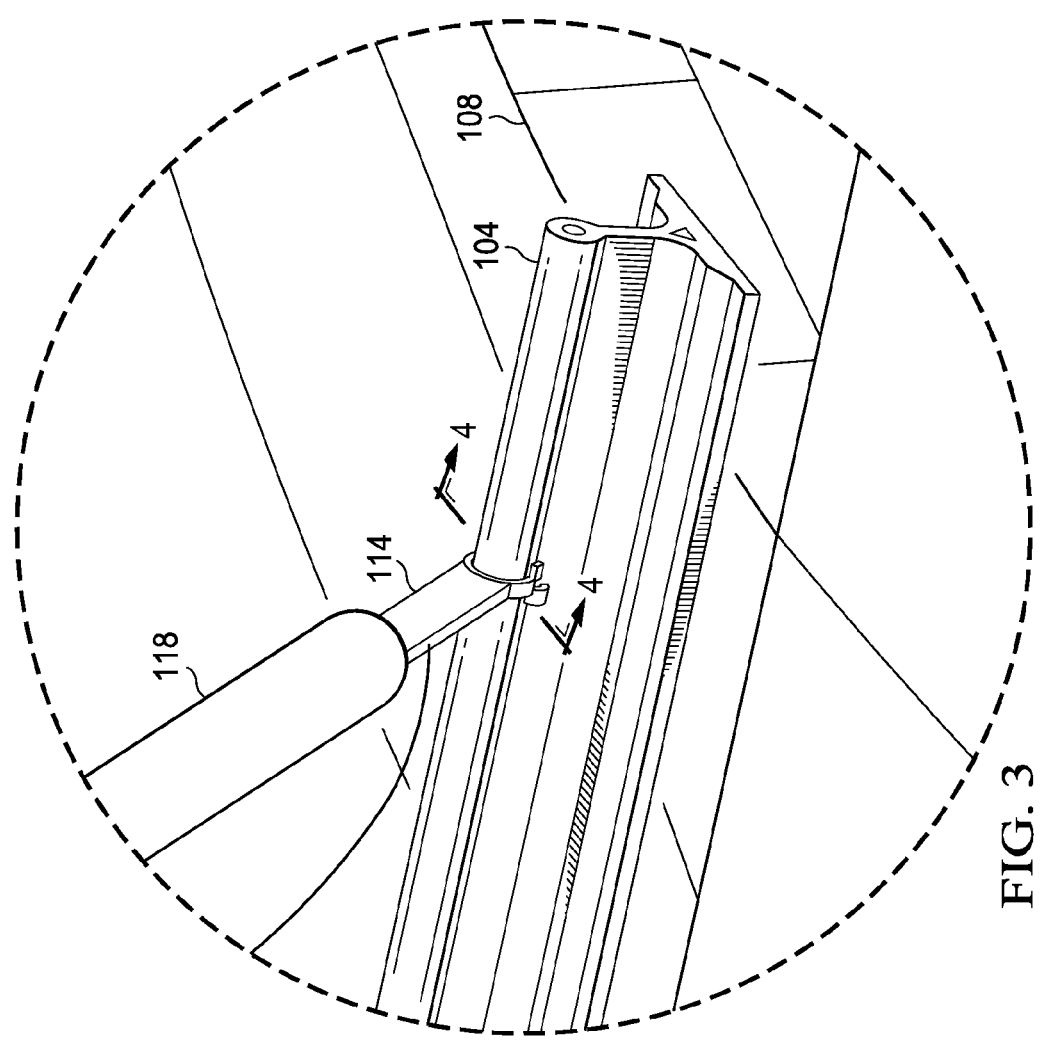
FIG. 3 is an illustration of an inspection unit positioned relative to a stiffener in accordance with an illustrative embodiment.

In these illustrative examples, inspection unit 112 and inspection unit 114 are each positioned over a section of stiffener 104 to cover and inspect a section of stiffener 104. The inspection of the sections by inspection unit 112 and inspection unit 114 may be made without multiple passes of each section. As a result, inspection unit 112 and inspection unit 114 may be moved along stiffener 104 in the direction of arrow 117 to perform the inspection of stiffener 104 in this particular example. A more detailed illustration of inspection unit 112 and stiffener 104 in section 119 is shown in FIG. 3.

The data generated by inspection unit 112 and inspection unit 114 is sent to computer 120 for processing. Inspection unit 112 sends data over wireless communications link 122 to computer 120. Inspection unit 114 sends the data over cable 124 to computer 120.

The illustration of inspection environment 100 in FIGS. 1A and 1B is only meant to be one illustrative example of an inspection environment in which an illustrative embodiment may be implemented. For example, an inspection environment in accordance with an illustrative embodiment may be implemented for use during maintenance, refurbishment, upgrades, or other operations that may be performed on an aircraft or other type platform.

Turning next to FIG. 2, an illustration of a block diagram of an inspection environment is depicted in accordance with an illustrative embodiment. In this depicted example, inspection environment 100 in FIGS. 1A and 1B is an example of one implementation for inspection environment 200 in FIG. 2.

As depicted, inspection system 202 is configured to inspect test object 204 in platform 206. Platform 206 may be aircraft 210 in this example. In this manner, inspection system 202 may be an aircraft inspection system in this illustrative embodiment. Test object 204 may take many different forms and may be a part in platform 206. For example, test object 204 may be selected from one of a stiffener, a stringer, a spar, a rib, a web, a flange, or other suitable objects. Additionally, platform 206 may be selected from one of a mobile platform, a stationary platform, a land-based structure, an aquatic-based structure, a space-based structure, a surface ship, a tank, a personnel carrier, a train, a spacecraft, a space station, a satellite, a submarine, an automobile, a power plant, a bridge, a dam, a house, a manufacturing facility, a building, or other suitable platforms.

In this illustrative example, inspection system 202 includes ultrasonic inspection system 212. Ultrasonic inspection system 212 includes inspection unit 214, operator 216, and controller 218.

In this example, inspection unit 214 is configured to send sound signals 220 into test object 204 and receive response signals 222 generated in response to sound signals 220. Inspection unit 112 and inspection unit 114 in FIGS. 1A and 1B are examples of implementations of inspection unit 214. In the illustrative examples, sound signals 220 may have any frequency configured to allow sound signals 220 to travel within test object 204. In these illustrative examples, sound signals 220 may be ultrasonic sound signals.

As depicted, inspection unit 214 comprises structure 224 and curved transducer array 226. Structure 224 is configured to hold or support curved transducer array 226. In particular, structure 224 is physically associated with curved transducer array 226. When one component is "physically associated" with another component, the association is a physical association in the depicted examples. For example, a first component, structure 224, may be considered to be physically associated with a second component, curved transducer array 226, by being secured to the second component, bonded to the second component, mounted to the second component, welded to the second component, fastened to the second component, and/or connected to the second component in some other suitable manner. The first component also may be connected to the second component using a third component. The first component may also be considered to be physically associated with the second component by being formed as part of the second component, an extension of the second component, or both.

Structure 224 may be rigid, flexible, or some combination thereof. Structure 224 may be comprised of different types of materials depending on the particular implementation.

For example, structure 224 may be comprised of a material selected from at least one of a metal, aluminum, a polycarbonate, rubber, or some other suitable type of material. As used herein, the phrase "at least one of", when used with a list of items, means different combinations of one or more of the listed items may be used and only one of each item in the list may be needed. For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A, one of item B, and ten of item C; four of item B and seven of item C; and other suitable combinations. The item may be a particular object, thing, or a category. In other words, at least one of means any combination of items and number of items may be used from the list but not all of the items in the list are required.

Curved transducer array 226 is comprised of transducers 228 arranged in an array. In the illustrative example, curved transducer array 226 has shape 230. As depicted, shape 230 is configured to cover non-planar surface 232 of test object 204.

Curved transducer array 226 has curved section 234. In some illustrative examples, curved transducer array 226 may have planar section 236.

In operation, curved transducer array 226 is configured to send sound signal 238 in sound signals 220 from first portion 240 of curved transducer array 226 through test object 204 to second portion 242 of curved transducer array 226. Sound signal 238 is received as response signal 244 in response signals 222. Sound signal 238 is a through-transmission when sound signal 238 is transmitted by first portion 240 of curved transducer array 226 and received as response signal 244 at second portion 242 of curved transducer array 226.

In this illustrative example, operator 216 is configured to position inspection unit 214 relative to test object 204. Additionally, operator 216 may move inspection unit 214 relative to test object 204 to perform inspection of test object 204.

Operator 216 may take various forms. For example, human operator 116 and robotic operator 118 in FIGS. 1A and 1B are examples of implementations for operator 216.

Controller 218 is configured to control the operation of transducers 228 in curved transducer array 226 and may be implemented in software, hardware, firmware or a combination of thereof. When software is used, the operations performed by controller 218 may be implemented in program code configured to run on a processor unit. When firmware is used, the operations performed by controller 218 may be implemented in program code and data and stored in persistent memory to run on a processor unit. When hardware is employed, the hardware may include circuits that operate to perform the operations in controller 218.

In the illustrative examples, the hardware may take the form of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

As depicted, controller 218 may be located in computer system 246. In some examples, controller 218 is in a location remote to inspection unit 214. In yet other illustrative examples, controller 218 may be physically associated with structure 224 in inspection unit 214.

During operation, controller 218 is configured to cause a transmission of sound signal 238 by first portion 240 of curved transducer array 226 and a reception of sound signal 238 as response signal 244 at second portion 242.

In the illustrative examples, controller 218 may change which of transducers 228 form first portion 240 and second portion 242. In other words, controller 218 may select different transducers in transducers 228 to send sound signals 220 and receive response signals 222.

In this manner, controller 218 may cause different transducers in transducers 228 in curved transducer array 226 to send sound signals 220 and receive response signals 222. As a result, the sending of sound signals 220 and the reception of response signals 222 may be controlled to sweep or scan the portions of test object 204 covered by curved transducer array 226.

As depicted, controller 218 may be configured to control transducers 228 such that sound signals 220 are transmitted in the form of beam 248. Beam 248 is configured to not converge at any particular point when traveling through test object 204. This generation of sound signals 220 is in contrast to other curved transducer arrays that use convergence.

Response signal 244 and response signals 222 may be used to determine whether inconsistency 250 is present in test object 204. In these illustrative examples, inconsistency 250 may take various forms. For example, inconsistency 250 may be selected from one of a delamination, a void, an undesired level of porosity, or other types of inconsistencies.

The illustration of inspection environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in addition to or in place of a through-transmission of sound signals 220, response signals 222 may be signals generated from sound signals 220 reflecting from features or other structures within test object 204. For example, response signals 222 may be generated from a pulse-echo in which response signals 222 are generated from reflections of sound signals 220. These reflections may be generated from at least one of layers of composite materials, voids, pores, or other inconsistencies or features in test object 204. Further, with pulse-echo, response signals 222 may be detected by other portions of transducers 228 in curved transducer array 226 used to send sound signals 220 other than the portion of transducers 228 in curved transducer array 226 that sends sound signals 220.

In another illustrative example, operator 216 may not be considered part of inspection system 202. In still other illustrative examples, one or more inspection units in addition to inspection unit 214 may be present in inspection system 202. Further, inspection system 202 may include other types of inspection systems in addition to ultrasonic inspection system 212. For example, ultrasonic inspection system 212 may include an eddy current inspection system, an x-ray inspection system, or other types of inspection systems in addition to ultrasonic inspection system 212.

Turning now to FIG. 3, an illustration of an inspection unit positioned relative to a stiffener is depicted in accordance with an illustrative embodiment. In this illustrative example, a more detailed view of section 119 with inspection unit 114 and stiffener 104 is shown.

As can be seen in this view, inspection unit 114 includes housing 300. Housing 300 is an example of an implementation for structure 224 in FIG. 2 and is physically associated with a curved transducer array (not shown) that is located within housing 300.

Figure 4:
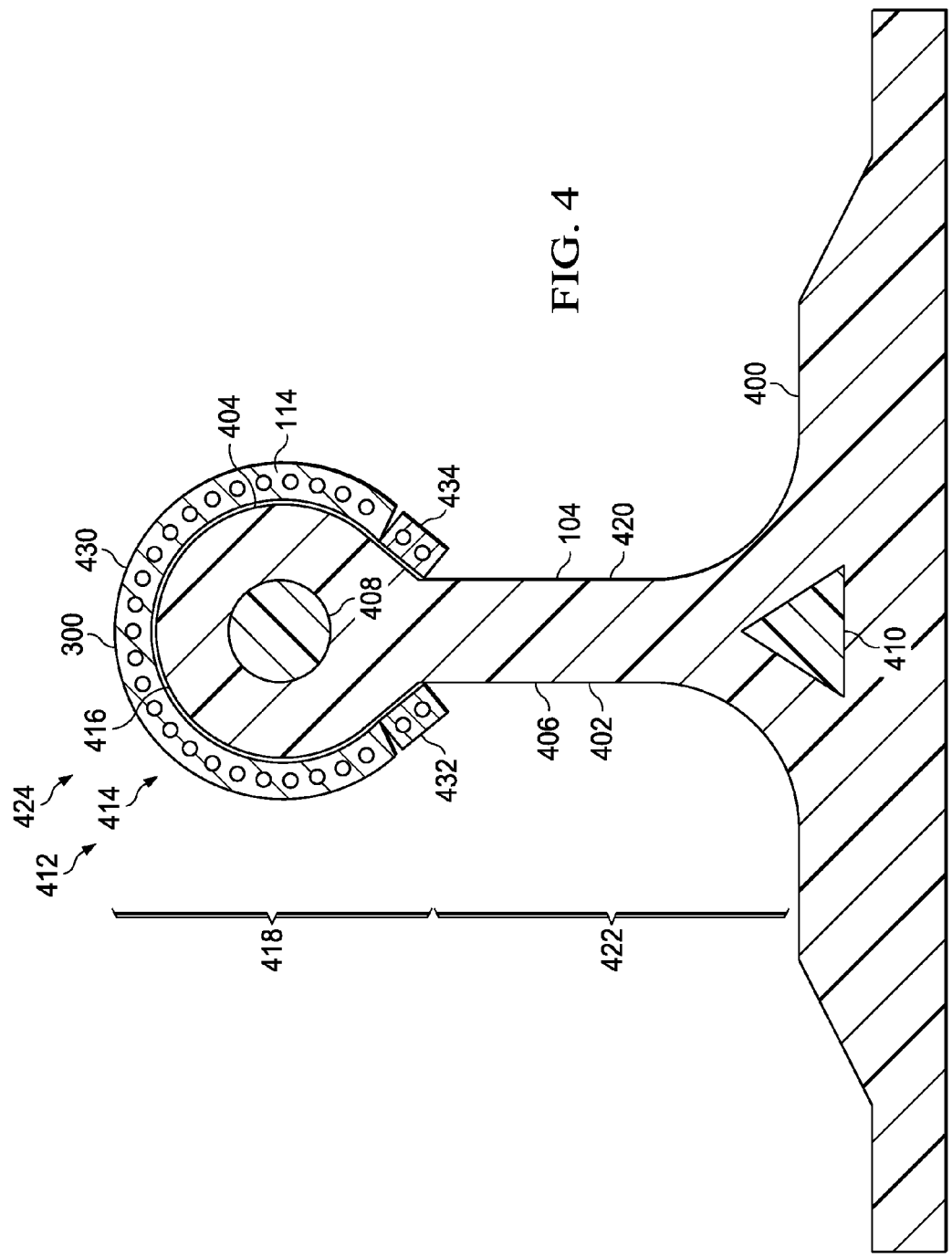
FIG. 4 is an illustration of a cross-sectional view of an inspection unit with a curved transducer array in accordance with an illustrative embodiment.

With reference now to FIG. 4, an illustration of a cross-sectional view of an inspection unit with a curved transducer array is depicted in accordance with an illustrative embodiment. In this illustrative example, a cross-sectional view of inspection unit 114 positioned relative to stiffener 104 is shown taken along lines 4-4 in FIG. 3.

In this view, base 400, web 402, and bulb 404 are shown for stiffener 104. In the illustrative example, stiffener 104 is a composite structure comprised of layers of composite material 406 that has been folded over each other and cured.

In forming stiffener 104, noodle 408 and noodle 410 are placed within layers of composite material 406 to aid in forming a desired shape for base 400 and bulb 404. Noodle 408 and noodle 410 may be comprised of layers of composite material that have an elongate shape.

As depicted, inspection unit 114 includes curved transducer array 412 within housing 300. As can be seen, curved transducer array 412 is comprised of transducers 414. In the illustrative example, transducers 414 are configured to send and receive sound signals. In particular, transducers 414 may be implemented using ultrasonic transducers.

In this example, curved transducer array 412 has a shape that is configured to cover non-planar surface 416 in section 418 for stiffener 104. Non-planar surface 416 is in contrast to surface 420 in section 422 for stiffener 104.

A non-planar surface is present in this illustrative example when two surfaces opposite to each other on an object are not planar to each other. In other illustrative examples, a first surface may be curved while a second surface opposite to the first surface is planar. For example, the first surface is a non-planar surface. In other words, the surface does not have to be curved on both sides or all the way around.

In this illustrative example, curved transducer array 412 includes transducers 414 located in curved segment 430, planar segment 432 and planar segment 434 of housing 300. In these illustrative examples, curved segment 430 may be offset relative to planar segment 432 and planar segment 434. Although transducers 414 may be located in planar segments in addition to a curved segment, transducers 414 are still referred to as curved transducer array 412. When planar segment 432 and planar segment 434 are offset from curved segment 430, transducers 414 may send and receive sound signals through bulb 404 such that inspection of all portions of bulb 404 may take place.

As depicted, curved segment 430, planar segment 432, and planar segment 434 are separate pieces physically connected to each other to form housing 300. In some illustrative examples, these segments may be implemented using a single continuous segment having a curved portion and planar portions.

Figure 5:
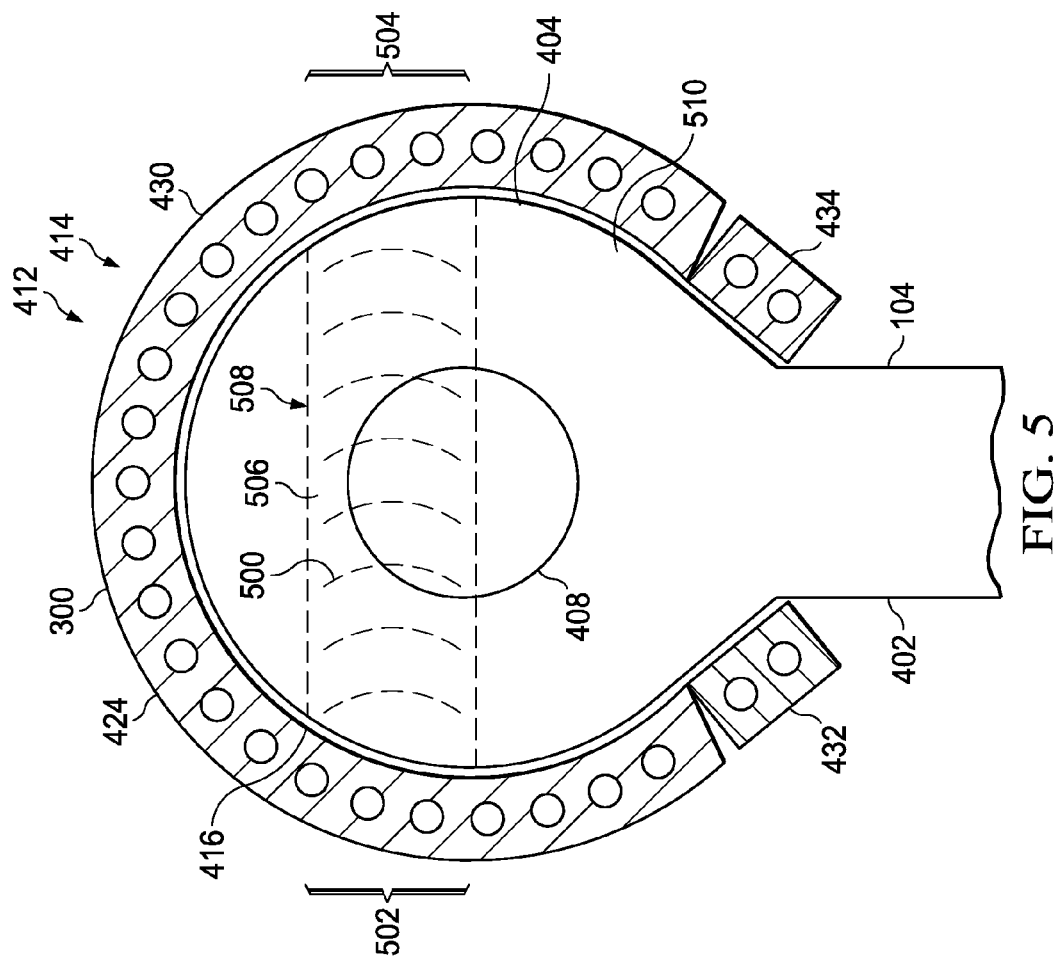
FIG. 5 is an illustration of sound signals sent into a stiffener in accordance with an illustrative embodiment.

With reference now to FIG. 5, an illustration of sound signals sent into a stiffener is depicted in accordance with an illustrative embodiment. In this illustrative example, curved transducer array 412 is configured to send sound signals 500 from first portion 502 of transducers 414 in curved transducer array 412 through bulb 404 in stiffener 104 to second portion 504 of transducers 414 in curved transducer array 412.

Second portion 504 of transducers 414 is configured to detect the response generated by sound signals 500. Sound signals 500 form the response when received by second portion 504 of transducers 414. As depicted, first portion 502 of transducers 414 in curved transducer array 412 is configured to send sound signals 500 in the form of beam 506. These types of transmissions of sound signals 500 form a through-transmission for use in determining whether an inconsistency is present in bulb 404.

In this illustrative example, sound signals 500 may be changed while traveling through layers of composite material 406 and noodle 408 in bulb 404. When an inconsistency is present, the change in sound signals 500 detected as a response by second portion 504 may be analyzed to identify the presence of the inconsistency.

As depicted, area 508 within inspection region 510 is covered by beam 506. Transducers 414 selected for first portion 502 and second portion 504 may be changed. The change in first portion 502 and second portion 504 may be made to inspect other areas in inspection region 510. In the illustrative examples, transducers 414 may be selected to perform an inspection using a pulse-echo technique.

Figure 6:
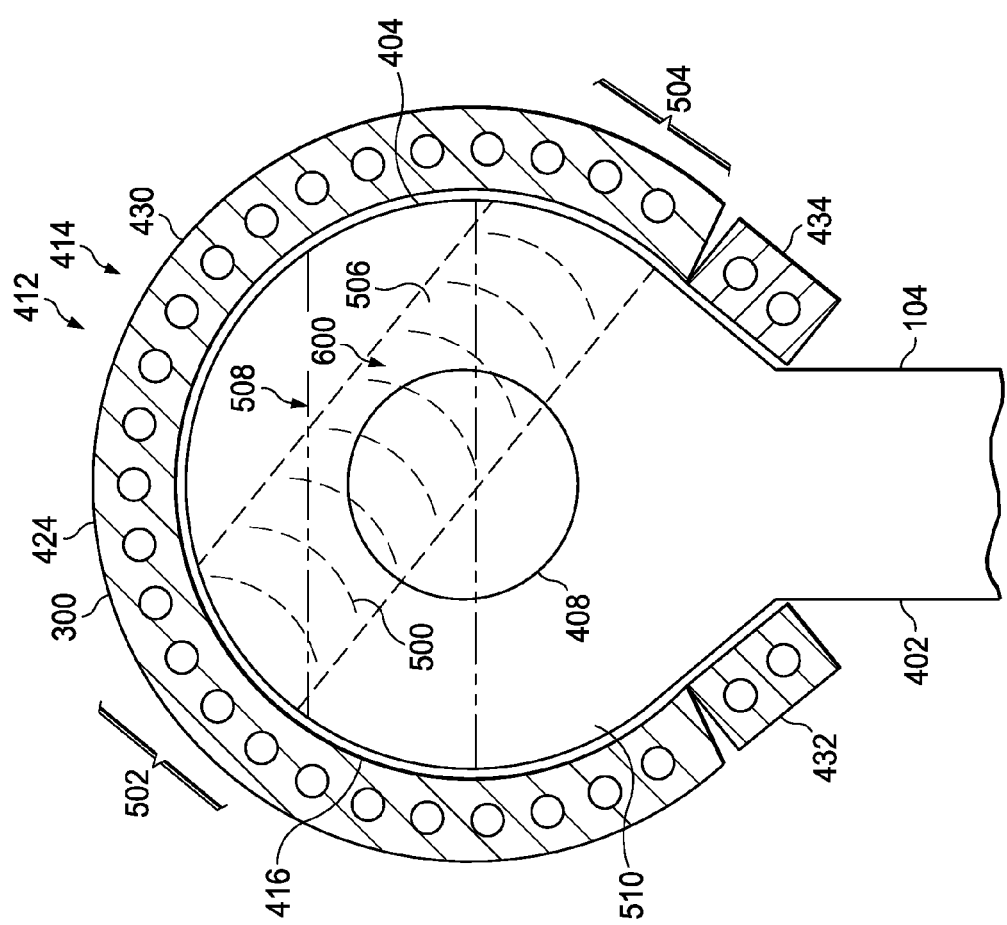
FIG. 6 is another illustration of sound signals sent into a stiffener in accordance with an illustrative embodiment.

Turning now to FIG. 6, another illustration of sound signals sent into a stiffener is depicted in accordance with an illustrative embodiment. In this example, first portion 502 and second portion 504 have been changed. Sound signals 500 in beam 506 are transmitted from first portion 502 through inspection region 510 and are received as a response by second portion 504. In this position, beam 506 covers area 600.

In this manner, first portion 502 and second portion 504 may be moved to allow for scanning of inspection region 510 within bulb 404. As a result, beam 506 of sound signals 500 may rotate, or otherwise move, to cover substantially all of inspection region 510 within bulb 404.

Figure 7:
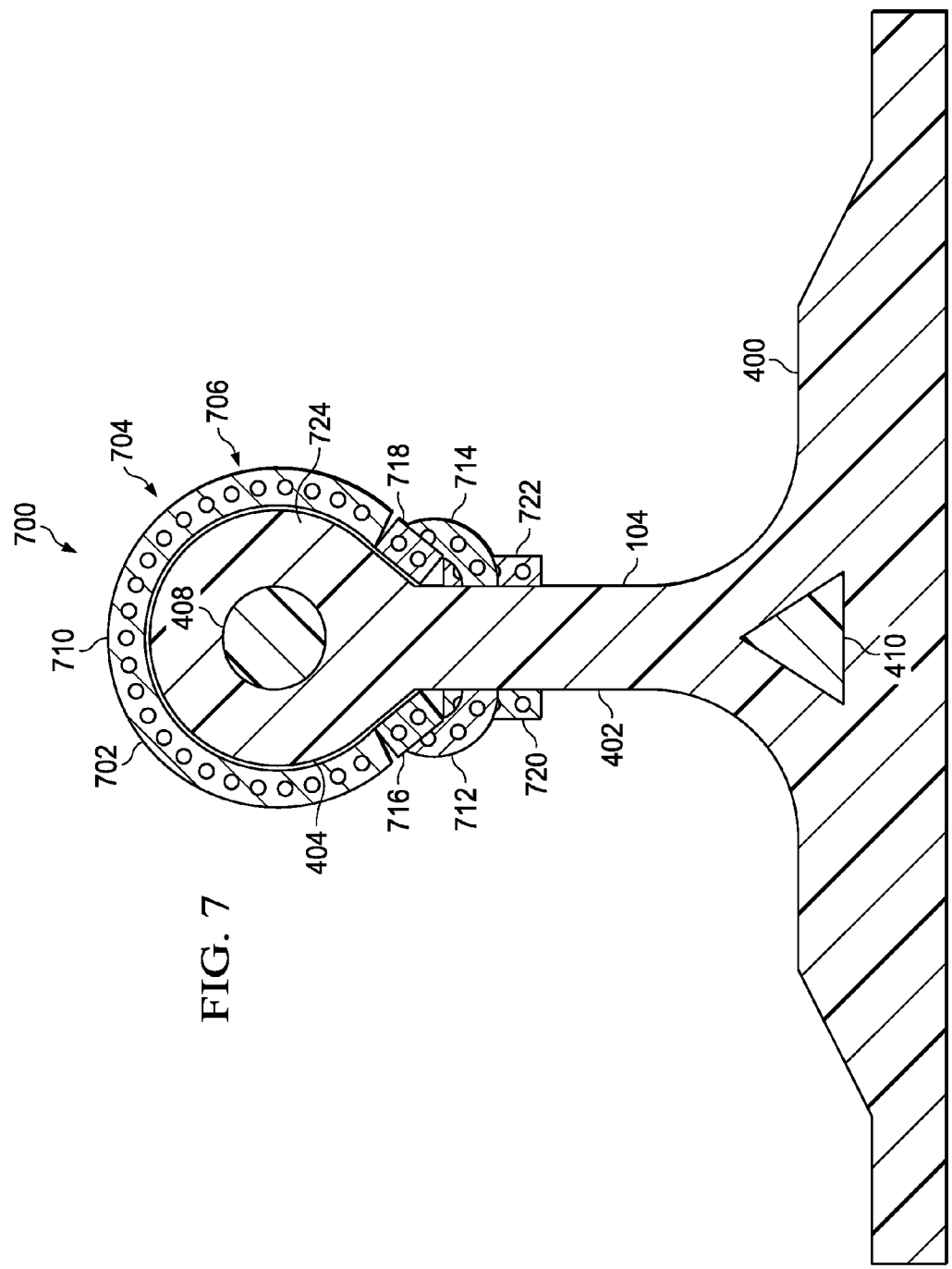
FIG. 7 is an illustration of an inspection unit in accordance with an illustrative embodiment.

Turning now to FIG. 7, an illustration of an inspection unit is depicted in accordance with an illustrative embodiment. A cross-sectional view of inspection unit 700 is positioned on bulb 404 of stiffener 104. As depicted, inspection unit 700 is an example of another configuration for inspection unit 214 in FIG. 2.

In this illustrative example, inspection unit 700 includes housing 702 with curved transducer array 704. Curved transducer array 704 is comprised of transducers 706.

Transducers 706 are located within segments that form housing 702. As can be seen, transducers 706 are located in curved segment 710, curved segment 712, curved segment 714, planar segment 716, planar segment 718, planar segment 720, and planar segment 722. Curved segment 712 overlaps planar segment 716 and curved segment 714 overlaps planar segment 718. In this illustrative example, these different segments are offset relative to each other.

With curved segment 712, curved segment 714, planar segment 720 and planar segment 722, additional coverage may be provided for inspection region 724. In this illustrative example, inspection region 724 for stiffener 104 is larger than inspection region 510 in FIG. 5. In this example, inspection region 724 also includes a portion of web 402.

Figure 8:
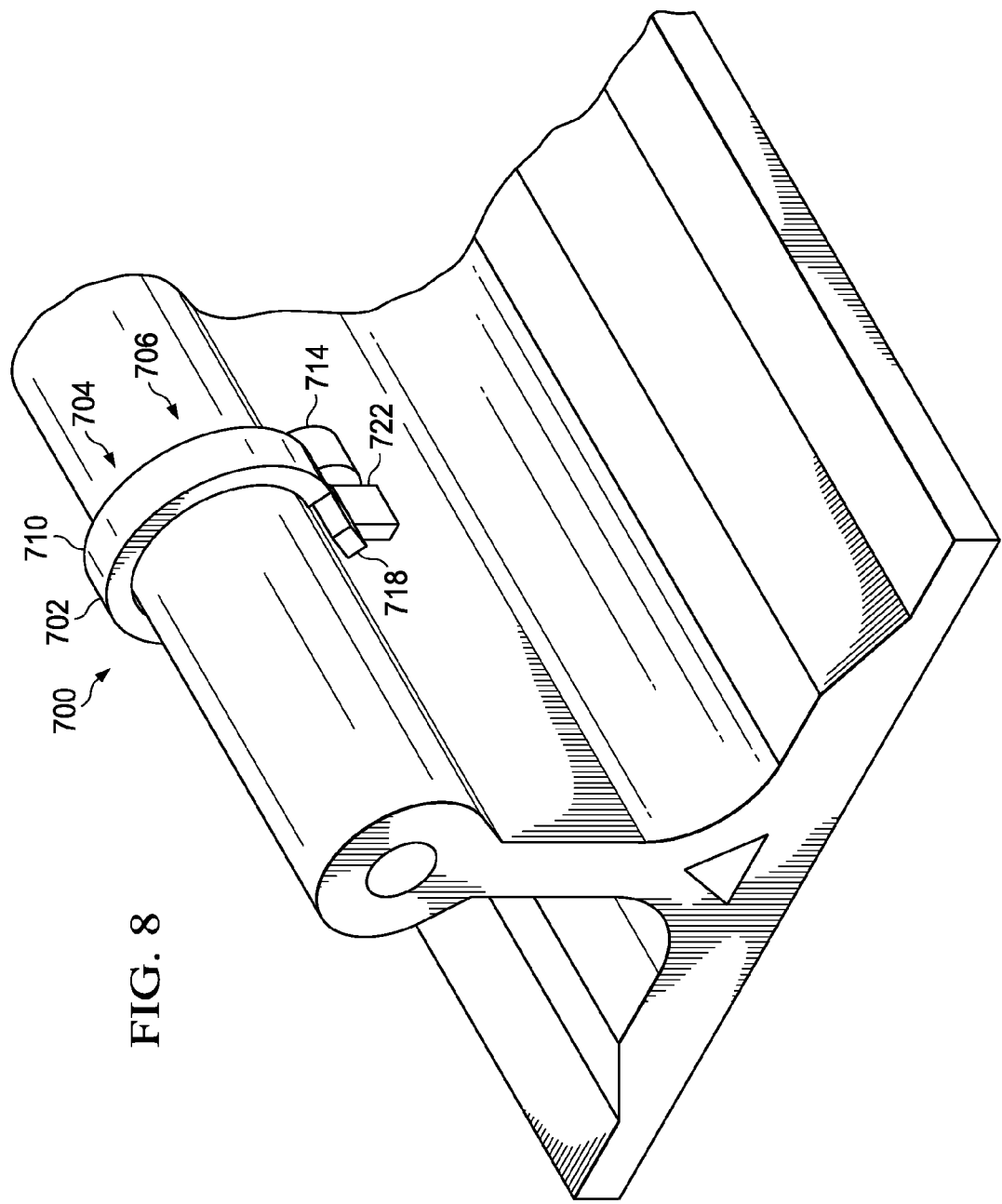
FIG. 8 is an illustration of a perspective view of an inspection unit on a stiffener in accordance with an illustrative embodiment.

Turning now to FIG. 8, an illustration of a perspective view of an inspection unit on a stiffener is depicted in accordance with an illustrative embodiment. In this view of inspection unit 700, the offset between curved segment 710, curved segment 712, curved segment 714, planar segment 716, planar segment 718, planar segment 720, and planar segment 722 is shown more clearly.

Figure 9:
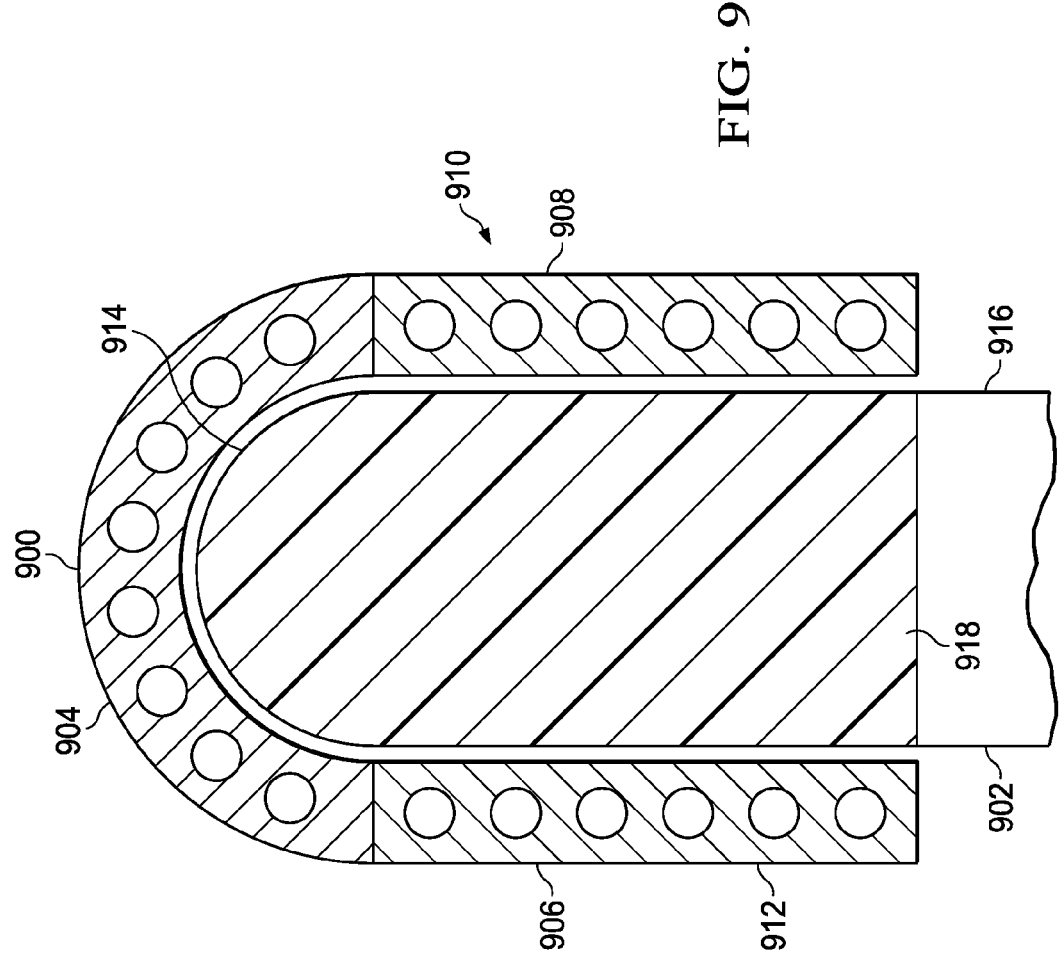
FIG. 9 is an illustration of a cross-sectional view of an inspection unit on a stiffener in accordance with an illustrative embodiment.

With reference now to FIG. 9, an illustration of a cross-sectional view of an inspection unit on a stiffener is depicted in accordance with an illustrative embodiment. As depicted, a cross-sectional view of inspection unit 900 on stiffener 902 is shown.

In this illustrative example, inspection unit 900 is comprised of curved segment 904, planar segment 906, and planar segment 908. These segments form a housing for transducers 910 in curved transducer array 912.

In this example, stiffener 902 does not have a bulb shape. Instead, bull nose 914 is present at the end of web 916 for stiffener 902.

Curved segment 904 has a shape configured to cover bull nose 914. Planar segment 906 and planar segment 908 are configured to cover a portion of web 916 for stiffener 902. With curved segment 904, planar segment 906, and planar segment 908, inspection area 918 may be inspected using sound signals to provide a desired amount of information about inspection area 918.

Figure 10:
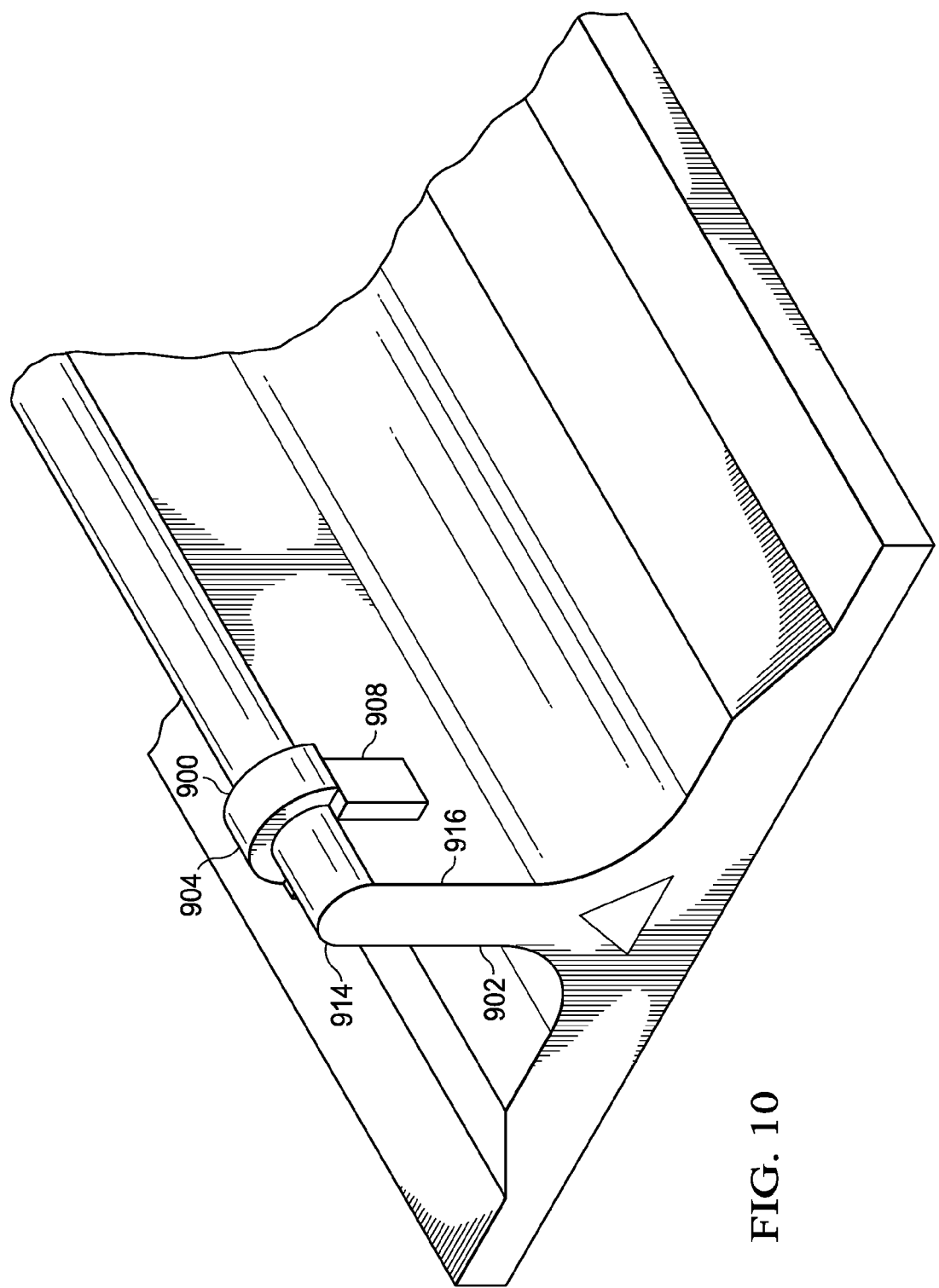
FIG. 10 is an illustration of an inspection unit on a stiffener in accordance with an illustrative embodiment.

Turning now to FIG. 10, an illustration of an inspection unit on a stiffener is depicted in accordance with an illustrative embodiment. In this illustrative example, a perspective view of inspection unit 900 is shown on stiffener 902. The arrangement of curved segment 904, planar segment 906, and planar segment 908 are shown more clearly in this view of inspection unit 900.

The illustration of the different inspection units in FIGS. 3-10 are only provided as examples of implementations for inspection unit 214 shown in block form in FIG. 2. These different physical implementations are not meant to limit the manner in which other inspection units may be implemented.

For example, although the different inspection units have been shown with the curved transducer array being located in multiple segments, other implementations may include a single housing having the desired shape for the curved transducer array. As yet another example, the inspection units may be used to inspect other test objects other than a stiffener. For example, the inspection units may be used to inspect a stringer, a spar, a rib, a web, a flange, or other suitable objects. In still another illustrative example, the different segments may be flexible rather than rigid.

An as yet another example, the curved transducer arrays in the different inspection units illustrated in FIGS. 3-10 may be used to perform other types of transmissions other than these transmissions. For example, the different curved transducer arrays may also be used to form inspections using a pulse-echo type of transmission and detection of sound signals in addition to or in place of these transmissions.

The different components shown in FIGS. 1 and 3-10 may be combined with components in FIG. 2, used with components in FIG. 2, or a combination of the two. Additionally, some of the components in FIGS. 1 and 3-10 may be illustrative examples of how components shown in block form in FIG. 2 can be implemented as physical structures.

Figure 11:
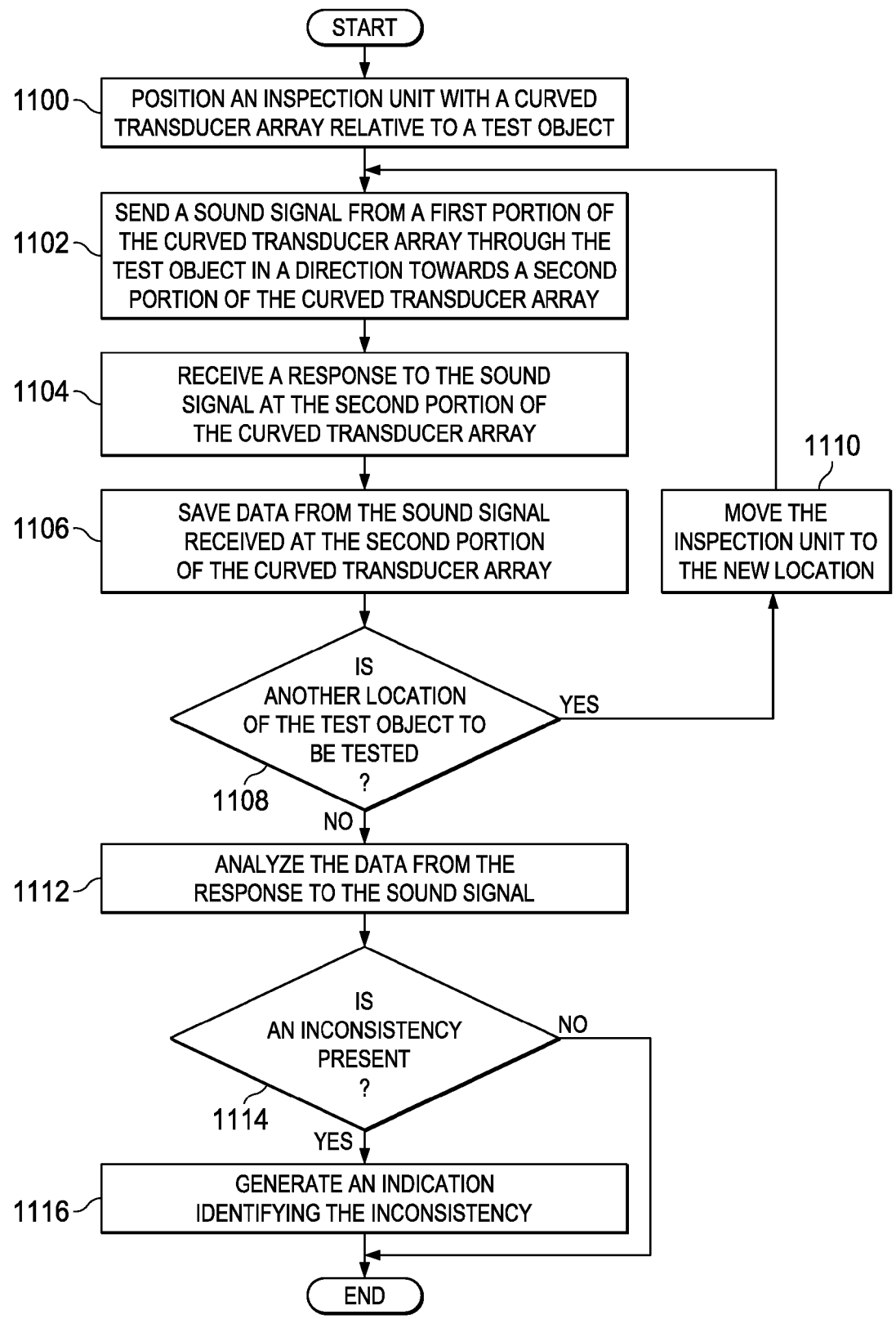
FIG. 11 is an illustration of a flowchart of a process for inspecting a test object in accordance with an illustrative embodiment.

With reference now to FIG. 11, an illustration of a flowchart of a process for inspecting a test object is depicted in accordance with an illustrative embodiment. The process illustrated in FIG. 11 may be implemented in inspection environment 200 in FIG. 2. In particular, the process may be implemented in ultrasonic inspection system 212 in FIG. 2.

The process begins by positioning an inspection unit with a curved transducer array relative to a test object (operation 1100). The process then sends a sound signal from a first portion of the curved transducer array through the test object in a direction towards a second portion of the curved transducer array (operation 1102). The curved transducer array has a shape that is configured to cover a non-planar surface of the test object. In operation 1102, the sound signal may be sent as a beam or part of a beam with other sound signals.

The process then receives a response to the sound signal at the second portion of the curved transducer array (operation 1104). Data from the sound signal received at the second portion of the curved transducer array is saved (operation 1106).

A determination is made as to whether another location of the test object is to be tested (operation 1108). If another location of the test object is to be tested, the inspection unit is moved to the new location (operation 1110), with the process then returning to operation 1102.

Otherwise, if another location of the test object is not to be tested, the process analyzes the data from the responses to the sound signal (operation 1112). A determination is then made as to whether an inconsistency is present (operation 1114).

If an inconsistency is present, an indication identifying the inconsistency is generated (operation 1116), with the process terminating thereafter. The indication may be, for example, a graphical indicator indicating the presence of the inconsistency on an image generated from the data. In other examples, the indication may be a message or other type of alert.

With reference again to operation 1114, the process also terminates if an inconsistency is not present.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 12:
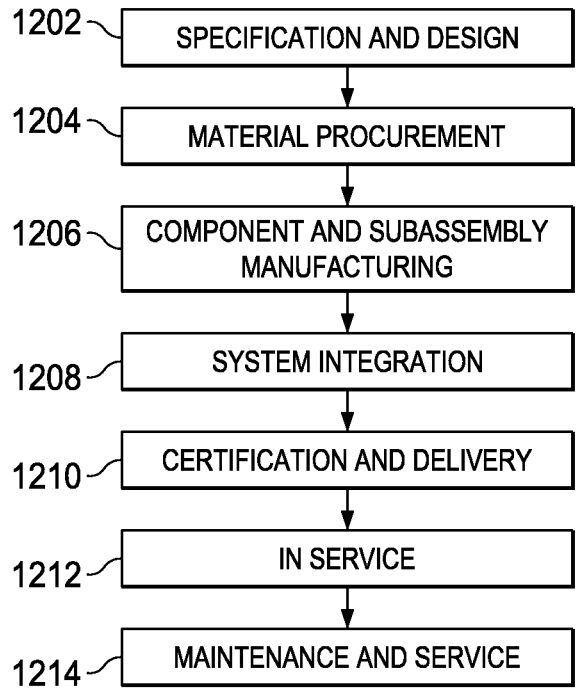
FIG. 12 is an illustration of an aircraft manufacturing and service method in accordance with an illustrative embodiment.
Figure 13:
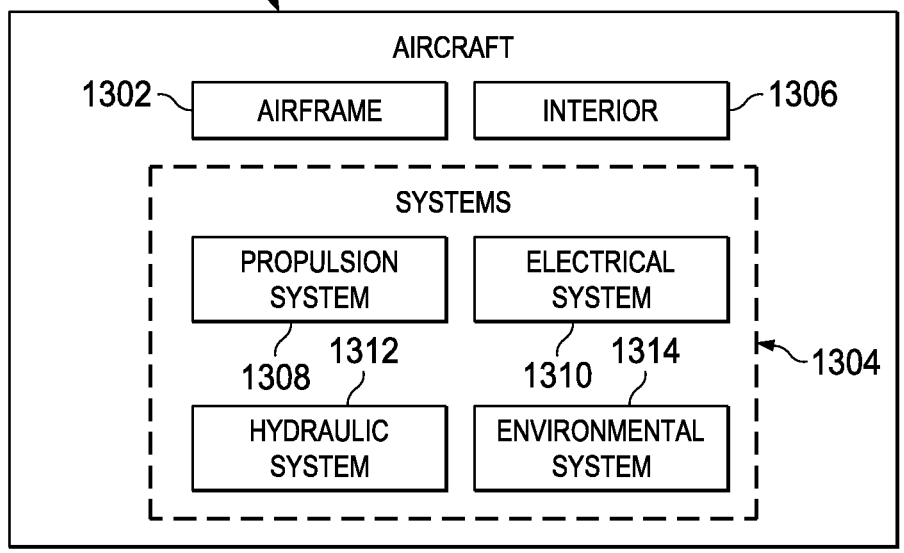
FIG. 13 is an illustration of an aircraft in which an illustrative embodiment may be implemented.

The illustrative embodiments of the disclosure may be described in the context of aircraft manufacturing and service method 1200 as shown in FIG. 12 and aircraft 1300 as shown in FIG. 13. Turning first to FIG. 12, an illustration of an aircraft manufacturing and service method is depicted in accordance with an illustrative embodiment. During pre-production, aircraft manufacturing and service method 1200 may include specification and design 1202 of aircraft 1300 in FIG. 13 and material procurement 1204.

During production, component and subassembly manufacturing 1206 and system integration 1208 of aircraft 1300 in FIG. 13 takes place. Thereafter, aircraft 1300 in FIG. 13 may go through certification and delivery 1210 in order to be placed in service 1212. While in service 1212 by a customer, aircraft 1300 in FIG. 13 is scheduled for routine maintenance and service 1214, which may include modification, reconfiguration, refurbishment, and other maintenance or service.

Each of the processes of aircraft manufacturing and service method 1200 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 13, an illustration of an aircraft is depicted in which an illustrative embodiment may be implemented. In this example, aircraft 1300 is produced by aircraft manufacturing and service method 1200 in FIG. 12 and may include airframe 1302 with plurality of systems 1304 and interior 1306. Examples of systems 1304 include one or more of propulsion system 1308, electrical system 1310, hydraulic system 1312, and environmental system 1314. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1200 in FIG. 12. In the illustrative examples, one or more apparatus embodiments, method embodiments, or a combination thereof may be utilized during production stages, such as component and subassembly manufacturing 1206 and system integration 1208 in FIG. 12. One or more apparatus embodiments, method embodiments, or a combination thereof may be utilized while aircraft 1300 is in service 1212 and/or during maintenance and service 1214 in FIG. 12. For example, inspection system 202 may be used to inspect parts in aircraft 1300 that are manufactured during component and subassembly manufacturing 1206. Inspection system 202 also may be used during maintenance and service 1214. Inspection system 202 may be used to inspect parts in use on aircraft 1300 during normal and routine maintenance and inspections. Inspection system 202 may also be used to inspect parts that are manufactured for replacement, upgrades, and refurbishment of aircraft 1300. The use of a number of the different illustrative embodiments may substantially expedite the assembly of and/or reduce the cost of aircraft 1300.

With one or more illustrative examples, inspections of test objects may be performed more easily as compared to currently available inspection systems. In the illustrative examples, a greater portion of an inspection region in a test object may be covered using a curved transducer array in accordance with an illustrative embodiment. For example, curved surfaces, ends with shapes such as a bulb, a bull nose, or other types of surfaces may be inspected.

As a result, a section of a composite structure may be inspected without performing multiple passes. For example, an inspection unit with transducers may cover the section and obtain information needed for analysis rather than moving the inspection unit over the section multiple times to take into account the non-planar surface in the composite structure.

This inspection may be applied to composite structures to identify inconsistencies. In particular, a level of porosity in a composite structure may be identified using inspection system 202. The response signals may be used to quantify porosity in an inspection region to determine whether the level of porosity is greater than a desired amount. In addition, inspection unit 214 may be used to inspect test objects other than test objects comprised of composite materials. Inspection unit 214 may be used to inspect a test object comprised of any material suitable to be tested using sound, such as ultrasonic signals.

Figure 14:
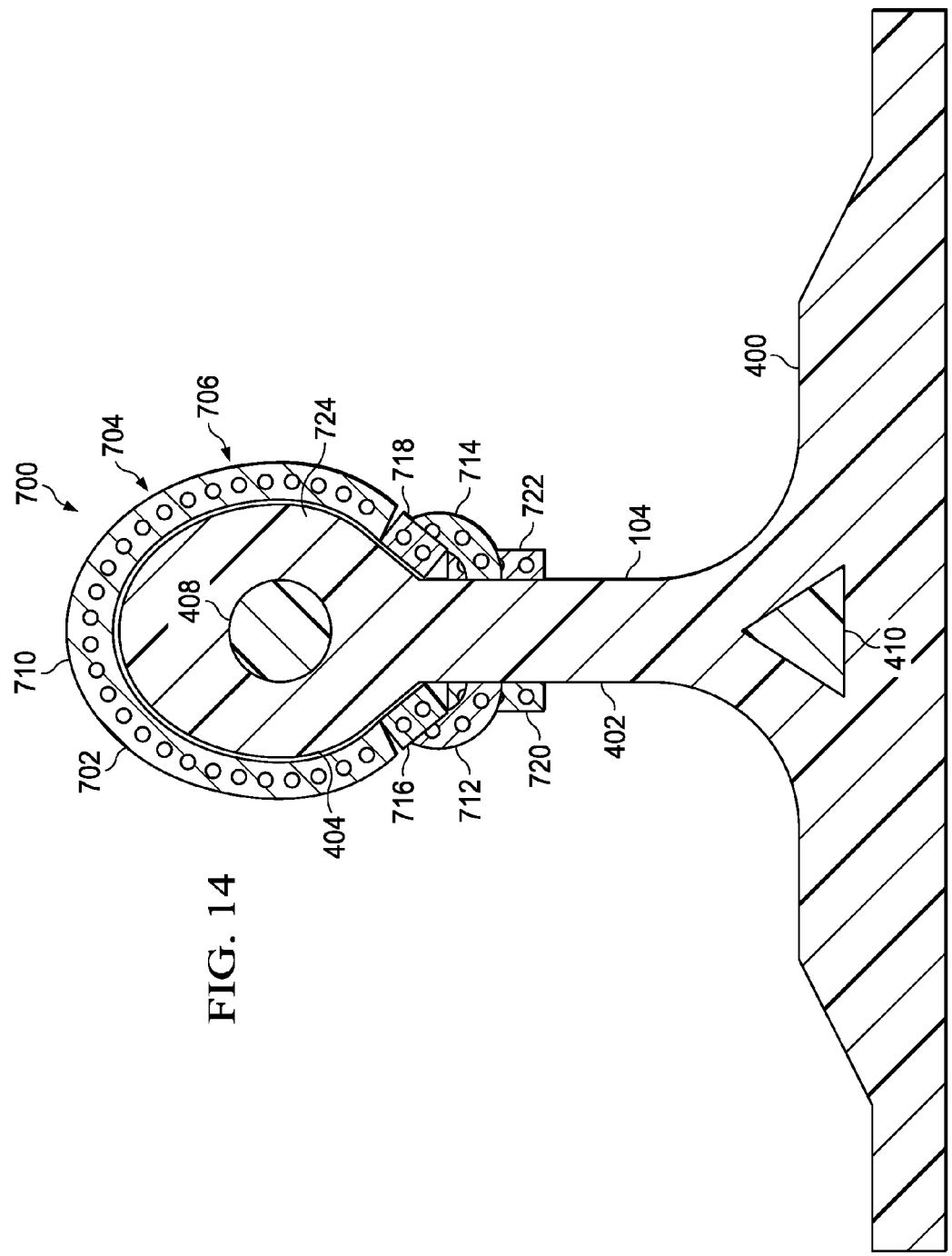
FIG. 14 is an illustration of an inspection unit in accordance with an illustrative embodiment.

FIG. 14 is an illustration of an inspection unit in accordance with an illustrative embodiment. FIG. 14 shows that bulb 404 and inspection unit 700 may be egg-shaped.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An inspection device comprising:
a curved transducer array configured to send a sound signal from a first portion of the curved transducer array through a test object that is at least partially bulb-shaped to a second portion of the curved transducer array, wherein the first portion is opposite the second portion relative to both a curve of the curved transducer array and the test object, and wherein a shape of the curved transducer array comprises:
a rounded portion configured to fit over an at least partially bulb-shape of the test object, the rounded portion including transducers;
a first planar section, connected to the rounded portion, configured to fit over a first planar-shape of the test object, the first planar section including transducers;
a second planar section, connected to the rounded portion opposite the first planar section, configured to fit over a second planar-shape of the test object, the second planar section including transducers; and
a first curved segment overlapping the first planar section and extending past the first planar section, the first curved segment including transducers; and
a second curved segment overlapping the second planar section and extending past the second planar section, the first curved segment opposite and separated from the second curved segment, the second curved segment including transducers.

2. The inspection device of claim 1, wherein the rounded portion is bulb shaped.

3. The inspection device of claim 1, wherein the rounded portion is egg shaped.

4. The inspection device of claim 1, wherein the rounded portion is bull nose shaped.

5. The inspection device of claim 1, wherein different curved portions of the curved transducer array are additionally configured to perform a pulse-echo type of transmission and detection of sound signals.

6. The inspection device of claim 1 further comprising:
a computer in communication with the curved transducer array; and
a display device in communication with the computer, wherein the computer is configured to interpret the sound signal and to command the display device to display an image of any imperfections in the test object.

7. The inspection device of claim 1, wherein the shape of the curved transducer array further comprises:
a third planar section connected to the first planar section and extending away from the first planar section at a first angle, the third planar section including transducers; and
a fourth planar section connected to the second planar section and extending away from the second planar section at a second angle, the fourth planar section including transducers.

8. The inspection device of claim 7, wherein the rounded portion is bulb shaped.

9. The inspection device of claim 7, wherein the rounded portion is egg shaped.

10. The inspection device of claim 7, wherein the rounded portion is bull nose shaped.

11. The inspection device of claim 7, wherein different curved portions of the curved transducer array are additionally configured to perform a pulse-echo type of transmission and detection of sound signals.

12. The inspection device of claim 7, further comprising:
a computer in communication with the curved transducer array; and
a display device in communication with the computer, wherein the computer is configured to interpret the sound signal and to command the display device to display an image of any imperfections in the test object.

13. The inspection device of claim 7, wherein the test object is a stiffener and the at least partially bulb shaped configuration of the stiffener comprises, at least in part, a bulb-shaped cross section connected to a planar cross section that extends from the bulb-shaped section, the curved transducer array being configured to fit over the stiffener such that the rounded portion, first planar section, and second planar section together conform to the bulb-shaped cross section, and such that the first curved segment, the second curved segment, the third planar section, and the fourth planar section together conform to the planar cross-section.

14. The inspection device of claim 13, wherein the rounded portion is bulb shaped.

15. The inspection device of claim 13, wherein the rounded portion is egg shaped.

16. The inspection device of claim 13, wherein the rounded portion is bull nose shaped.

17. The inspection device of claim 13, wherein different curved portions of the curved transducer array are additionally configured to perform a pulse-echo type of transmission and detection of sound signals.

18. The inspection device of claim 13 further comprising:
a computer in communication with the curved transducer array; and
a display device in communication with the computer, wherein the computer is configured to interpret the sound signal and to command the display device to display an image of any imperfections in the test object.

* * * * *